(12) United States Patent
Alharmi et al.

(10) Patent No.: US 10,245,133 B2
(45) Date of Patent: Apr. 2, 2019

(54) MEDICAL DEVICE FOR CONSTRICTING A BODY PASSAGE AND A METHOD THEREOF

(71) Applicant: University of Dammam, Dammam (SA)

(72) Inventors: Rawan A. Rahman Alharmi, Isa Town (BH); Rayan Mohammed Ali Alabduljabbar, AlQatif (SA); Nusaybah Nasser Alnaim, Dammam (SA)

(73) Assignee: University of Dammam, Dammam (SA)

( * ) Notice: Subject to any disclaimer, the term of this patent is extended or adjusted under 35 U.S.C. 154(b) by 195 days.

(21) Appl. No.: 15/241,322

(22) Filed: Aug. 19, 2016

(65) Prior Publication Data
US 2017/0252141 A1 Sep. 7, 2017

Related U.S. Application Data

(60) Provisional application No. 62/301,974, filed on Mar. 1, 2016.

(51) Int. Cl.
*A61F 2/00* (2006.01)
*A61B 5/00* (2006.01)
*A61B 5/20* (2006.01)

(52) U.S. Cl.
CPC ............ *A61F 2/0018* (2013.01); *A61B 5/205* (2013.01); *A61B 5/4836* (2013.01); *A61F 2210/009* (2013.01); *A61F 2220/0075* (2013.01); *A61F 2230/0065* (2013.01); *A61F 2250/001* (2013.01); *A61F 2250/0002* (2013.01); *A61F 2250/008* (2013.01)

(58) Field of Classification Search
CPC ....... A61B 5/076; A61B 5/205; A61B 5/4836; A61B 5/686; A61B 5/6874; A61F 2/0018; A61F 2210/009; A61F 2220/0075; A61F 2230/0065; A61F 2250/0001; A61F 2250/0002; A61F 2250/001; A61F 2250/008
USPC ...................................... 600/29–32
See application file for complete search history.

(56) References Cited

U.S. PATENT DOCUMENTS 2,455,859 A * 12/1948 Foley ................. A61F 2/0054
128/DIG. 25
2,533,924 A * 12/1950 Foley ................. A61F 2/0054
128/885

(Continued)

FOREIGN PATENT DOCUMENTS

EP 2957257 A1 12/2015
KR 1431052 B1 8/2014

(Continued)

*Primary Examiner* — Navin Natnithithadha
*Assistant Examiner* — Sunita Reddy
(74) *Attorney, Agent, or Firm* — Oblon, McClelland, Maier & Neustadt, L.L.P.

(57) ABSTRACT

A plurality of bodies that attract one another are provided for implanting in a patient, specifically around a body passage of the patient. For example, the body passage may be the urethra, and the plurality of bodies may be implanted around the outside of the urethra, and the bodies being substantially coaxial with the urethra. The attraction between adjacent bodies may be provided by a magnetic or a mechanical force.

15 Claims, 4 Drawing Sheets

(56) References Cited

U.S. PATENT DOCUMENTS

| | | | | |
|---|---|---|---|---|
| 3,815,576 | A * | 6/1974 | Balaban | A61F 2/004 128/DIG. 25 |
| 4,053,952 | A * | 10/1977 | Goldstein | A61F 2/0018 128/DIG. 25 |
| 4,994,019 | A * | 2/1991 | Fernandez | A61F 2/0036 128/DIG. 25 |
| 6,022,312 | A * | 2/2000 | Chaussy | A61F 2/0022 600/29 |
| 6,135,945 | A * | 10/2000 | Sultan | A61B 5/0031 128/DIG. 25 |
| 6,432,038 | B1 * | 8/2002 | Bakane | A61F 2/0022 600/29 |
| 6,460,262 | B1 * | 10/2002 | Cabak | A61B 5/1076 33/511 |
| 2003/0060893 | A1 * | 3/2003 | Forsell | A61F 2/0036 623/23.65 |
| 2003/0144575 | A1 * | 7/2003 | Forsell | A61F 2/0036 600/29 |
| 2003/0144648 | A1 * | 7/2003 | Forsell | A61F 2/004 604/544 |
| 2004/0173219 | A1 * | 9/2004 | Bakane | A61F 2/0054 128/885 |
| 2005/0251182 | A1 * | 11/2005 | Bachmann | A61F 5/0053 606/157 |
| 2005/0283235 | A1 * | 12/2005 | Kugler | A61B 17/12009 623/14.13 |
| 2007/0185371 | A1 * | 8/2007 | Bortolotti | A61B 17/12 600/29 |
| 2009/0012351 | A1 * | 1/2009 | Anderson | A61B 17/1322 600/30 |
| 2010/0179376 | A1 * | 7/2010 | Kassab | A61F 2/0018 600/30 |
| 2010/0204803 | A1 * | 8/2010 | Tozzi | A61F 2/0036 623/23.72 |
| 2012/0184980 | A1 * | 7/2012 | Anderson | A61F 2/0036 606/192 |
| 2012/0296157 | A1 * | 11/2012 | Tozzi | A61F 2/0036 600/30 |
| 2013/0096586 | A1 * | 4/2013 | Tozzi | A61F 2/0036 606/157 |
| 2013/0274546 | A1 * | 10/2013 | Anderson | A61F 2/004 600/31 |
| 2014/0088342 | A1 * | 3/2014 | Djurovic | A61F 5/003 600/30 |
| 2014/0371855 | A1 * | 12/2014 | Clement | A61F 2/0036 623/14.13 |
| 2014/0378746 | A1 * | 12/2014 | Mohammadi | A61F 2/0036 600/30 |
| 2015/0025303 | A1 * | 1/2015 | Deitch | A61F 2/004 600/31 |
| 2015/0045609 | A1 * | 2/2015 | Anderson | A61F 2/004 600/31 |
| 2015/0051443 | A1 * | 2/2015 | Kassab | A61F 2/04 600/37 |
| 2015/0105859 | A1 * | 4/2015 | Frigstad | A61F 2/0036 623/14.13 |
| 2015/0230904 | A1 * | 8/2015 | Shabat | A61F 2/004 600/31 |
| 2015/0320536 | A1 * | 11/2015 | Deitch | A61F 2/0036 600/30 |
| 2016/0074196 | A1 * | 3/2016 | Forsell | A61F 2/004 600/31 |
| 2016/0220341 | A1 * | 8/2016 | Anderson | A61F 2/004 |
| 2017/0065402 | A1 * | 3/2017 | Tozzi | A61F 2/0036 |

FOREIGN PATENT DOCUMENTS

| | | |
|---|---|---|
| WO | WO 2009/048375 A1 | 4/2009 |
| WO | WO 2010/042048 A1 | 4/2010 |

* cited by examiner

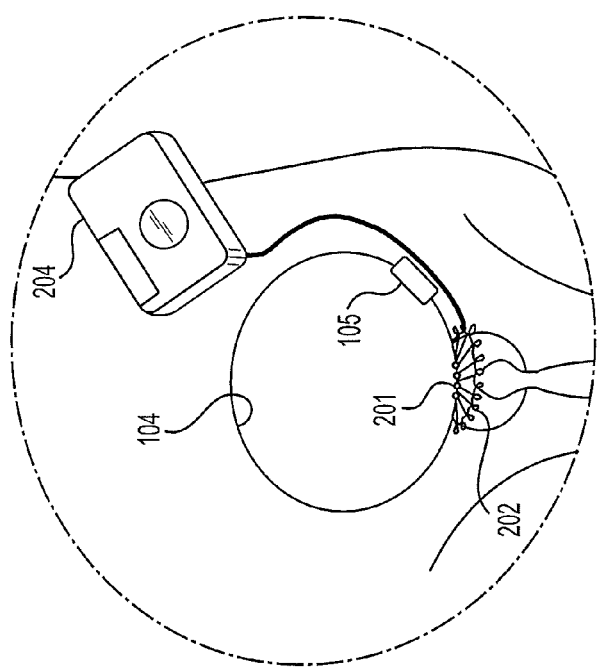
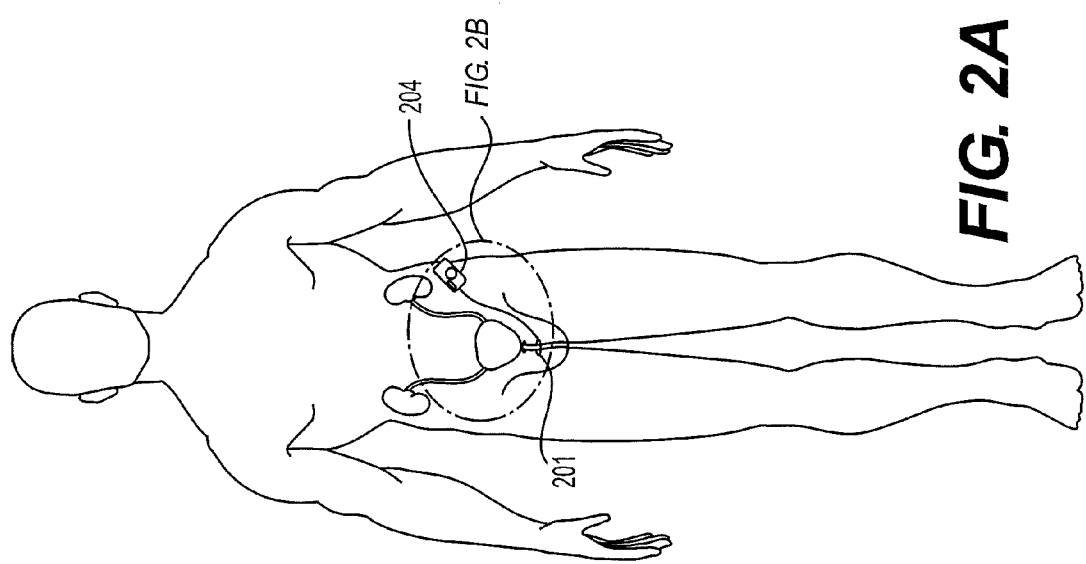

MEDICAL DEVICE FOR CONSTRICTING A BODY PASSAGE AND A METHOD THEREOF

RELATED APPLICATIONS

This application claims the priority of the filing date of U.S. Provisional Patent Application No. 62/301,974 filed Mar. 1, 2016, the disclosure of which is hereby incorporated herein by reference.

BACKGROUND OF THE INVENTION

Field of the Invention

This disclosure is directed to a medical device for improving or modifying the performance of a body passage. The body passage may be the urinary tract, and the medical device may be employed for treating urinary incontinence.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

A variety of human ailments arise from the weakening of tissues surrounding body lumens and cavities due to disease, trauma, advancing age, or combinations of these causes. A condition known as gastroesophageal reflux disease (GERD) arises when the lower esophageal sphincter weakens and permits the contents of the stomach to move back into the esophagus. Urinary incontinence arises in both men and women with varying degrees of severity and from different causes. In men, the condition frequently occurs as a result of prostatectomies which damage the urinary sphincter. In women, the condition typically arises after pregnancy where stretching of the structure supporting the urinary tract can weaken the urethra. Similarly, fecal incontinence can occur when the anal sphincter becomes weakened and ceases to function properly.

A number of approaches have been developed for treating urinary incontinence. For example, the American Medical Systems (AMS) 800™ is a medical device that serves as an artificial sphincter. It mimics the physiological function of the urinary sphincter. The device is made of silicone and is fluid-filled. It has a cuff, a pressure-regulating balloon, a pump and a control button. Although this device is widely used, there have been many medical complications, such as erosion and/or migration of the cuff and infection, which resulted in removal of the device (Sajadi, K. P. et al., Artificial Urinary Sphincter Placement; American Medical Systems, AMS 800® Artificial Urinary Sphincter, 2014; Ratan, H. L., Summerton, D. J., Wilson, S. K., Terry, T. R., Development and Current Status of the AMS 800 Artificial Urinary Sphincter, European Association of Urology, 2006, 117-128—each incorporated herein by reference in its entirety).

In view of the foregoing, the objective of the present disclosure is to provide a medical device for constricting a body passage and improving bodily functions. A method of using the medical device is also disclosed.

SUMMARY OF THE DISCLOSURE

The foregoing description is intended to provide a general introduction and summary of the present disclosure and is not intended to be limiting in its disclosure unless otherwise explicitly stated. The presently preferred embodiments, together with further advantages, will be best understood by reference to the following detailed description taken in conjunction with the accompanying drawings.

A first aspect of the disclosure relates to a medical device, comprising: (i) a plurality of bodies arranged in an annular array and configured to surround a body passage so that each body contacts the body passage for constricting at least a portion of the body passage, where the plurality of bodies comprise a magnetic material and are elastically connected to one another, (ii) a pressure sensor to sense a pressure on a bladder, and (iii) a computer in communication with the pressure sensor and the plurality of bodies, where the computer controls the movement of the plurality of bodies toward or away from a center of the annular array with a magnetic force in response to signals from the pressure sensor.

In one embodiment, the plurality of bodies is connected by an elastic and flexible wire.

In one embodiment, the magnetic material is present in an embedded magnetic core.

In one embodiment, the embedded magnetic core is coated with a biocompatible material.

In one embodiment, the body passage is the urethra.

In one embodiment, the pressure sensor measures a pressure in the bladder and communicates the pressure to the computer which alerts a patient when the pressure rises above a predetermined threshold value.

In one embodiment, the computer is electrically connected to both the pressure sensor and the plurality of bodies.

In one embodiment, each body is in the form of a bead.

In one embodiment, the medical device of the first aspect further comprises a ring with a coil of wire around the ring, which has an inner diameter larger than a largest diameter of the annular array and is electrically connected to the computer.

In one embodiment, the inner diameter of the ring is 1-5 mm larger than the largest diameter of the annular array.

In one embodiment, both the ring and the coil of wire comprise iron.

In one embodiment, the computer controls an electrical current that affects a magnetization of the ring to attract each body toward the ring and away from the center of the annular array.

In one embodiment, the medical device further comprises a plurality of links, where each link extends between each body and the ring to allow each body to move toward or away from the center of the annular array.

In one embodiment, each link is a spring.

A second aspect of the disclosure relates to a medical device, comprising: (i) a plurality of bodies surrounding a body passage so that each body contacts the body passage for constricting at least a portion of the body passage, wherein the plurality of bodies are elastically connected to one another and enclose a space therebetween, (ii) a pressure sensor to sense a pressure on a bladder, and (iii) a computer electrically connected to the pressure sensor and the plurality of bodies, where the computer controls and electrical current that affects a magnetic force that affects a size of the space in response to signals from the pressure sensor.

In one embodiment, each body is in the form of a plate.

In one embodiment, the medical device has a first rectangular plate and a second rectangular plate positioned at opposing portions of a curved surface of the body passage.

In one embodiment, the computer controls a magnetic polarity of the first plate.

A third aspect of the disclosure relates to a method for treating urinary incontinence in a patient, comprising: (i) implanting the plurality of bodies of the medical device of the first aspect around a portion of the urinary tract, (ii) implanting the pressure sensor of the medical device of the first aspect to detect a pressure of the bladder with the pressure sensor, (iii) communicating a detected pressure to the computer of the medical device of the first aspect, which alerts the patient when the detected pressure rises above a predetermined threshold value, and (iv) expanding the annular array to discharge urine through the urethra when the detected pressure exceeds the predetermined threshold value, and (v) contracting the annular array to prevent urine discharge from the urethra when the detected pressure is less than the predetermined threshold value.

A fourth aspect of the disclosure relates to a method for treating urinary incontinence in a patient, comprising: (i) implanting the plurality of bodies of the medical device of the second aspect around a portion of the urinary tract, (ii) implanting the pressure sensor of the medical device of the second aspect to detect a pressure of the bladder with the pressure sensor, (iii) communicating a detected pressure to the computer of the medical device of the second aspect, which alerts the patient when the detected pressure rises above a predetermined threshold value, and (iv) increasing the size of the space to allow urine to discharge through the urethra when the detected pressure exceeds the predetermined threshold value, and (v) decreasing the size of the space to prevent urine discharge from the urethra when the detected pressure is less than the predetermined threshold value.

BRIEF DESCRIPTION OF THE DRAWINGS

FIG. 2A shows the locations of the pressure sensor and the plurality of bodies in an annular array according to another embodiment of the medical device.

FIG. 2B is an exploded view of the location of the annular array shown in FIG. 2A.

DETAILED DESCRIPTION OF THE DISCLOSURE

Embodiments of the present disclosure will now be described more fully hereinafter with reference to the accompanying drawings, in which some, but not all embodiments of the disclosure are shown.

Figure 1B:
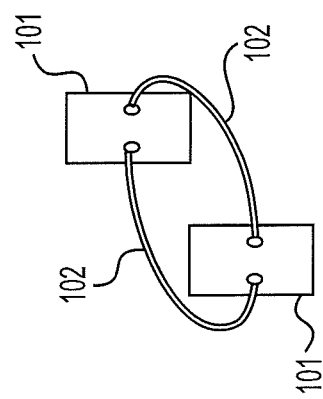
FIG. 1B is an exploded view of the plurality of bodies shown in FIG. 1A.
Figure 1A:
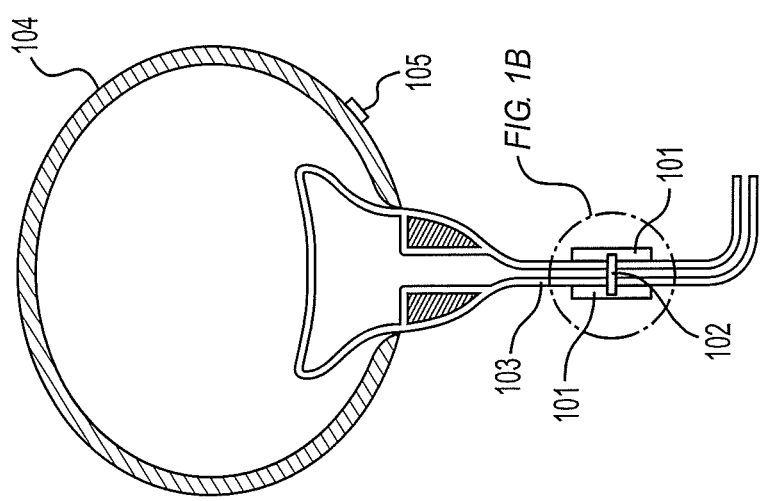
FIG. 1A shows the locations of the pressure sensor and the plurality of bodies according to an embodiment of the medical device.

Referring to FIGS. 1 and 2, the first aspect of the disclosure relates to a medical device, comprising: (i) a plurality of bodies 201 arranged in an annular array and configured to surround a body passage so that each body contacts the body passage for constricting at least a portion of the body passage, where the plurality of bodies comprise a magnetic material and are elastically connected to one another, (ii) a pressure sensor 105 to sense a pressure on a bladder, and (iii) a computer 204 in communication with the pressure sensor and the plurality of bodies, where the computer controls the movement of the plurality of bodies toward or away from a center of the annular array with a magnetic force in response to signals from the pressure sensor.

The medical device may be employed for treating gastroesophageal reflux disease (GERD), urinary and/or bowel incontinence. Preferably, this medical device is employed to treat urinary incontinence of various etiologies, which include, but are not limited to aging, diabetes, neurological disorders and tumor growth along the urinary tract, for example, in locations such as the urethra, ureter, renal pelvis and/or bladder 104. In a preferred embodiment, the bodies are embedded in the walls of the body passage and their native surface does not protrude into the passage. For example, the bodies may be attached to the mucosa layer of the urethra because the layer may have sufficient mechanical strength to support the bodies.

Each body may take a form of a rectangular plate, a square plate, a cylinder, a disc or a bead which may be a sphere, a regular hexagon, an ellipsoid or a cube. Preferably, each bead is a sphere. A diameter of each body ranges from 0.5-4 mm, preferably 0.5-3 mm, more preferably 0.5-1.5 mm. As used herein, the term "diameter" refers to the greatest possible distance measured from a vertex of a polygon through the center of the face to the vertex on the opposite side. For spheres and ellipsoids, "diameter" refers to the greatest possible distance measured from one point on the sphere/ellipsoid through the center of the sphere/ellipsoid to a point directly across from it.

When each body is a cylinder, a rectangular plate or an ellipsoid, the body may be substantially parallel to the longitudinal axis of the body passage. When each body is a rectangular plate or a disc, the body may be arranged with a face with the larger surface area in contact with the body passage.

Each body is attracted to the adjacent body in the annular array such that the annular array exhibits self-limiting annular contraction. Once all of the adjacent bodies in a closed loop are in contact with one another, the loop cannot get any smaller and the interior of the structure inherently remains open. The attraction between each body may be provided by a magnetic force or, preferably, a spring force. The attraction between adjacent bodies may be provided by pre-stressed tension springs 102 between the bodies. The bodies can move apart by stretching the spring, which will then urge the bodies to move back into contact with one another. Springs may be of an elastic and flexible biocompatible material such as an elastic metal or an elastic polymer. As used herein, the term "biocompatible material" refers to a material that is compatible with living tissue by not being toxic, injurious, or physiologically reactive with biochemical solids, liquids, and gases and not causing immunological response. Non-limiting examples of biocompatible materials include non-reactive metals and/or alloys, such as stainless steel, titanium, platinum, nickel titanium alloy and tantalum, and polymers such as PTFE, polyurethane and polyamide. Preferably, titanium is employed. There may be a spring between each body and the spring may be outside of the body. The exterior of the body may have an attachment point, such as a loop and/or a hook, for the spring, which may be attached to the body with a hook, a clamp and/or a knot. In one embodiment, there is a spring between each body and each spring threads through the center of each body. In an alternative embodiment, there is a continuous spring which connects all the bodies. This spring passes through each body and may have two free ends (e.g., in the form of loops) that can be connected to one another to form an annular prosthesis. In one embodiment, the bodies are not at fixed locations along the circumference of the spring. In a preferred embodiment, some or all of the bodies are secured to the spring at predetermined locations along its circumference so that when the plurality of bodies is stretched apart to allow the passage of solids and/or fluids, the bodies are equally spaced along the circumference of the spring. The spring may comprise knots which are regularly spaced to secure the bodies to their predetermined locations.

The number of bodies is chosen to constrict the body passage to a constricted state in which the blood circulation in the constricted body passage is substantially unrestricted and the flow of solids and/or fluids is at least somewhat restricted relative to the body passage in an unconstricted state. The number of bodies may range from 2-20, preferably 4-12, more preferably 4-10. When all the bodies are in contact with one another, the diameter of the annular array ranges from 1-15 mm, preferably 4-12 mm, more preferably 4-10 mm. For adults, there are preferably 5-9 bodies, preferably 6-9 bodies, more preferably 7-9 bodies and the diameter of the annular array ranges from 5-9 mm, preferably 6-9 mm, more preferably 7-9 mm. For children and/or young adults, there are preferably 2-6 bodies, preferably 2-5 bodies, more preferably 3-5 bodies and the diameter of the annular array ranges from 2-6 mm, preferably 2-5 mm, more preferably 3-5 mm. The diameter of the annular array is the distance measured from the center of a first body to the center of a second body which is the furthest away from the first body. When the plurality of bodies are stretched apart to allow the passage of solids and/or fluids, the diameter of the annular array increases by 1-30% relative to the initial diameter of the annular array, preferably 5-20%, more preferably 10-15%. In one embodiment, the diameter of the expanded annular array ranges from 2-19.5 mm, preferably 5-15 mm, more preferably 5-12 mm.

Each body comprises a magnetic core which can be, but does not need to be biocompatible because the magnetic core is coated with the aforementioned biocompatible material. As used herein, "magnetic core" refers to a material which may have, or be charged with, magnetic energy. In some embodiments, a magnetic core may include two magnets with opposite polarities that attract one another. Preferably, a magnetic core may be a piece of a magnetically soft material that does not have polarities and can be magnetized in the presence of an external magnetic field and demagnetized in the absence of the external magnetic field. Non-limiting examples of magnetically soft materials include iron, alloys of iron and nickel, alloys of rare earth metals and commercially available materials such as Permalloy, HyMu and Mu-metal. A shape of the magnetic core may include, but is not limited to, a cube, a cuboid, a sphere, a cylinder, and a pyramid. Preferably, the shape of the magnetic core is the same as that of the body. A diameter of the magnetic core ranges from 0.1-3.5 mm, preferably 0.2-2 mm, more preferably 0.2-1 mm. A volume of the core is preferably 10-90% of the total volume of the body, preferably 30-70%, more preferably 40-50%.

In some embodiments, there is a ring 202 which comprises iron, and preferably made of medical grade stainless steel such as 316L and 316LVM. The inner diameter of the ring ranges from 2-20 mm, preferably 5.5-14.5 mm and is 1-5 mm larger than the largest diameter of the annular array to allow for the expansion of the annular array, preferably 1.5-2.5 mm. The thickness of the ring may range from 0.05-1 mm, preferably 0.05-0.5 mm, more preferably 0.05-0.2 mm. The ring provides a fixation for the annular array and may occupy at least a portion of the bulbous urethra 103 in males. In one embodiment, the annular array and the ring are implanted at the neck of the bladder 104 (FIG. 2B).

Figure 2C:
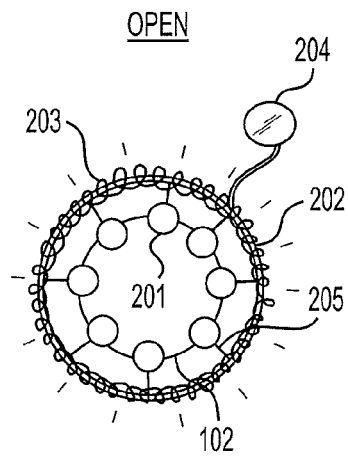
FIG. 2C shows the expansion of the annular array shown in FIGS. 2A and 2B.
Figure 2D:
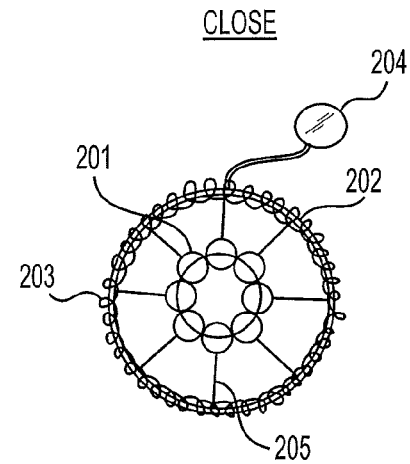
FIG. 2D shows the contraction of the annular array shown in FIGS. 2A and 2B to gently constrict the neck of the bladder.

There may be a plurality of links 205 extending between each body and an inner surface of the ring. Preferably, the link is a pre-stressed compression spring made of the aforementioned biocompatible elastic materials. The bodies can move toward the ring by compressing the spring (FIG. 2C), which will then urge the bodies to move back into contact with one another (FIG. 2D).

Figure 2E:
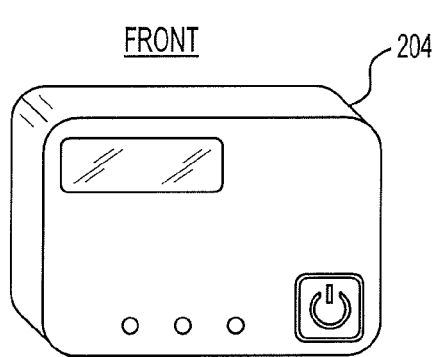
FIG. 2E shows the front view of an embodiment of the computer.
Figure 2F:
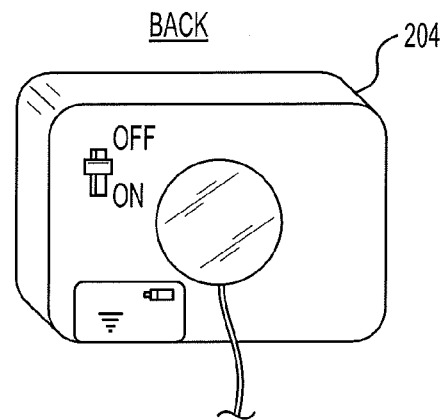
FIG. 2F shows the back view of the computer shown in FIG. 2E.

A coil of wire 203, preferably made of the aforementioned grades of stainless steel, may also be wound around the ring, which also serves as an electromagnet. The diameter of the wire ranges from 0.01-1 mm, preferably 0.025-0.2 mm, more preferably 0.025-0.1 mm. There may be 10-200 coils around the ring, preferably 50-150 coils, more preferably 80-120 coils. The coil of wire is electrically connected to the computer 204 (FIGS. 2E and 2F). Specifically, the coil of wire may be connected to a battery, preferably a rechargeable battery, in the computer. The computer controls an electrical current which runs through the coil of wire and affects the magnetization of the ring and its ability to attract the bodies in the annular array. For example, a resting state of the plurality of bodies is where the bodies are attracted towards one another and pulled towards the center of the annular array by springs or magnetic forces between the bodies. In this state, the body passage is constricted. In an activated state, the ring is magnetized and attracts the bodies away from the center of the annular array thus allowing the body passage to expand and permit the flow of solids and/or fluids. In one embodiment, a wireless connection is employed and the coil of wire may comprise an antenna configured to receive wireless power and electronics coupled to the antenna and configured to magnetize or demagnetize the ring (Tee, C. et al., US Patent Application 20140350348A1; Poon, A. et al., WIPO Patent Application WO2014071079 A1—each incorporated herein by reference in its entirety). The computer may be configured to provide wireless power to the antennae and configured to receive the data on the magnetization of the ring and the movement of the annular array.

A sensor is implanted to sense a physical parameter of the patient, such as the pressure in the bladder, or a parameter that relates to the pressure in the urinary tract. Many different types of sensors for sensing physical parameters may be used. Non-limiting examples of sensors include motion sensors for sensing motion, i.e. natural contractions, such as bladder contractions, pressure sensors for sensing pressure in the urethra, ureter, renal pelvis or bladder, strain sensors for sensing strain of the urethra, ureter, renal pelvis or bladder, flow sensors for sensing flow of urine, spectrophotometrical sensors, pH-sensors for sensing acidity or alkalinity of the urine in the urinary passageway and oxygen sensors for sensing the oxygen content of the urine in the urinary passageway. A sensor may be implanted on the exterior bladder wall. In one embodiment, a sensor is implanted on the interior bladder wall so that the sensor is in contact with the urine to measure, for example, the flow of urine, the pH and/or the oxygen content of urine.

Preferably, a pressure sensor 105, which monitors the bladder pressure chronically, is implanted in the wall of the bladder 104, for example, by employing conventional urological tools such as a cystoscope (Fletter, P. C. et al., The 6$^{th}$ International Conference on Networked Sensing System, 2009, 228-231—incorporated herein by reference in its entirety). Preferably, a sharp point of a hollow insertion tool pierces the mucosa and creates a small pocket in the submucosal area next to the bladder. The pressure sensor may be held in this space by the mucosa, which exhibits a sufficient mechanical strength to retain the pressure sensor (Fletter, P. C. et al., Proceedings of the ASME 2008 Summer Bioengineering Conference, 2008, 25-29—incorporated herein by reference in its entirety). These sensors may be placed inside or outside of the bladder and they undergo a conformational change as the bladder shape changes (Rajagopalan, S. et al., Sensors, 2008, 5081-5095; Gutierrez, C. A., Meng., E., Journal of Micromechanical Microengineering, 2010, 095028; Hung, C., Uday, T., Vaibhav, L., Ai-Ling, L., Yuan-Bo, P., Chiao, J., IEEE topical conference on biomedical wireless technologies, networks, and sensing systems (BioWireless), 2013—each incorporated herein by reference in its entirety). A length of the pressure sensor may range from 5-30 mm, preferably 10-20 mm, more preferably 15-20 mm. A width of the pressure sensor may range from 5-20 mm, preferably 5-10 mm, more preferably 8-10 mm. A height of the pressure sensor may range from 1-10 mm, preferably 3-7 mm, more preferably 4-6 mm. Non-limiting types of the pressure sensor include piezoresistive, capacitive, electromagnetic, piezoelectric, optical and potentiometric. Preferably, a MEMS piezoresistive pressure sensor is employed. The pressure sensor may be powered by a battery or external radio frequency sources (Young, D. J. et al., Lab Chip, 2015, 15, 4338-4347—incorporated herein by reference in its entirety). A pressure of the fluid exerted on the bladder may be measured through the urothelium and calibrated to account for attenuation from the tissue. The patient will be alerted when the pressure rises above a predetermined threshold value, which may range from 10-40 cm $H_2O$, preferably 20-40 cm $H_2O$, more preferably 25-35 cm $H_2O$.

The pressure sensor 105 is electrically connected to the computer 204. In one embodiment, a wireless pressure sensor is used (Tee, C. et al., US Patent Application 20140350348A1; Poon, A. et al., WIPO Patent Application WO2014071079 A1—each incorporated herein by reference in its entirety). The wireless pressure sensor may comprise an antenna configured to receive wireless power and electronics coupled to the antenna and configured to communicate the detected pressure to the computer. The computer may be configured to provide wireless power to the antennae of the wireless pressure sensor and configured to receive the detected pressure.

The computer 204 may include a clock mechanism for controlling the annular array to change the constriction of the urethra, for example, to increase or decrease the influence on the flow of urine during different time periods of the day. For example, the computer may be set to alert the patient to micturate at regular time intervals e.g. every 2 hours in the day and every 6 hours at night. In one embodiment, where a pressure sensor is employed, either the clock mechanism is employed for controlling the annular array provided that the detected pressure does not override the clock mechanism, or the pressure sensor is employed for controlling the annular array provided that the clock mechanism does not override the pressure sensor. Suitably, the computer produces an indication, such as a sound signal and/or displayed information and/or a vibration, in response to signals from the sensor. The computer may comprise a source of energy, such as a rechargeable battery, to magnetize the ring and hence move the plurality of bodies. The computer may be attached to the patient's clothes, preferably near the inguinal region, by clips to facilitate removal of the computer when necessary.

The computer may comprise an implantable and programmable internal control unit, such as a microprocessor, that directly controls the annular array in response to signals from the sensor. The internal control unit may be implanted subcutaneously or in the abdomen and may include the aforementioned clock mechanism. The internal control unit may comprise an implanted source of energy, such as a rechargeable battery, to magnetize the ring and hence move the plurality of bodies. Therefore, the internal control unit also works as an energy receiver, i.e., for transforming wireless energy into electric energy and charging the implanted source of energy (rechargeable battery) with the electric energy. In one embodiment, the internal control unit comprises at least one transceiver to transmit and receive wireless energy from the external control unit, the pressure sensor and/or the ring. For example, the transceiver in the internal control unit may send a signal to the external control unit in response to signals from the pressure sensor indicating a predetermined threshold value of pressure is reached.

The computer may further include an external control unit intended to be outside the patient's body, where the internal control unit is programmable by the external control unit. For example, the internal control unit may be programmable for controlling the annular array over time, suitably in accordance with an activity schedule program. The computer may comprise an external data communicator and an implantable internal data communicator communicating with the external data communicator, where the internal communicator feeds data related to the annular array and/or the pressure sensor back to the external data communicator or the external data communicator feeds data to the internal data communicator.

In one embodiment, the external control unit is in the form of a hand-held wireless remote control or be designed for an application in electronic devices such as a phone, a tablet and/or a watch. The wireless remote control may comprise at least one external signal transmitter or transceiver and at least one internal signal receiver or transceiver implantable in the patient. The wireless remote control preferably transmits at least one wireless control signal for controlling the internal control unit. The wireless control signal may comprise a frequency, amplitude, or phase modulated signal or a combination thereof. Alternatively, the wireless remote control transmits an electromagnetic carrier wave signal for carrying the control signal. The control signal may comprise one of the following: an electric field, a magnetic field, a combined electric and magnetic field. Alternatively, the control signal comprises an analogue signal, a digital signal, or a combination of an analogue and digital signal. The remote control may be adapted to set control parameters of the internal control unit from outside the patient without mechanically penetrating the patient. At least one of the control parameters, which is settable by the wireless remote control, is the predetermined threshold value of the bladder pressure. The wireless remote control may also be adapted to set the clock mechanism. The patient may use the remote control to control the annular array to adjust the constriction of the wall portion of the urethra, ureter, renal pelvis or bladder. Specifically, the remote control is operable by the patient to control the internal control unit to expand (turn on)

or contract (turn off) the annular array. Alternatively, however, the remote control may be replaced by a subcutaneously implanted push button that is manually switched by the patient between "on" and "off". Such a manually operable push button may also be provided in combination with the remote control as an emergency button to allow the patient to stop the operation of the apparatus in case of emergency or malfunction.

Figure 3:
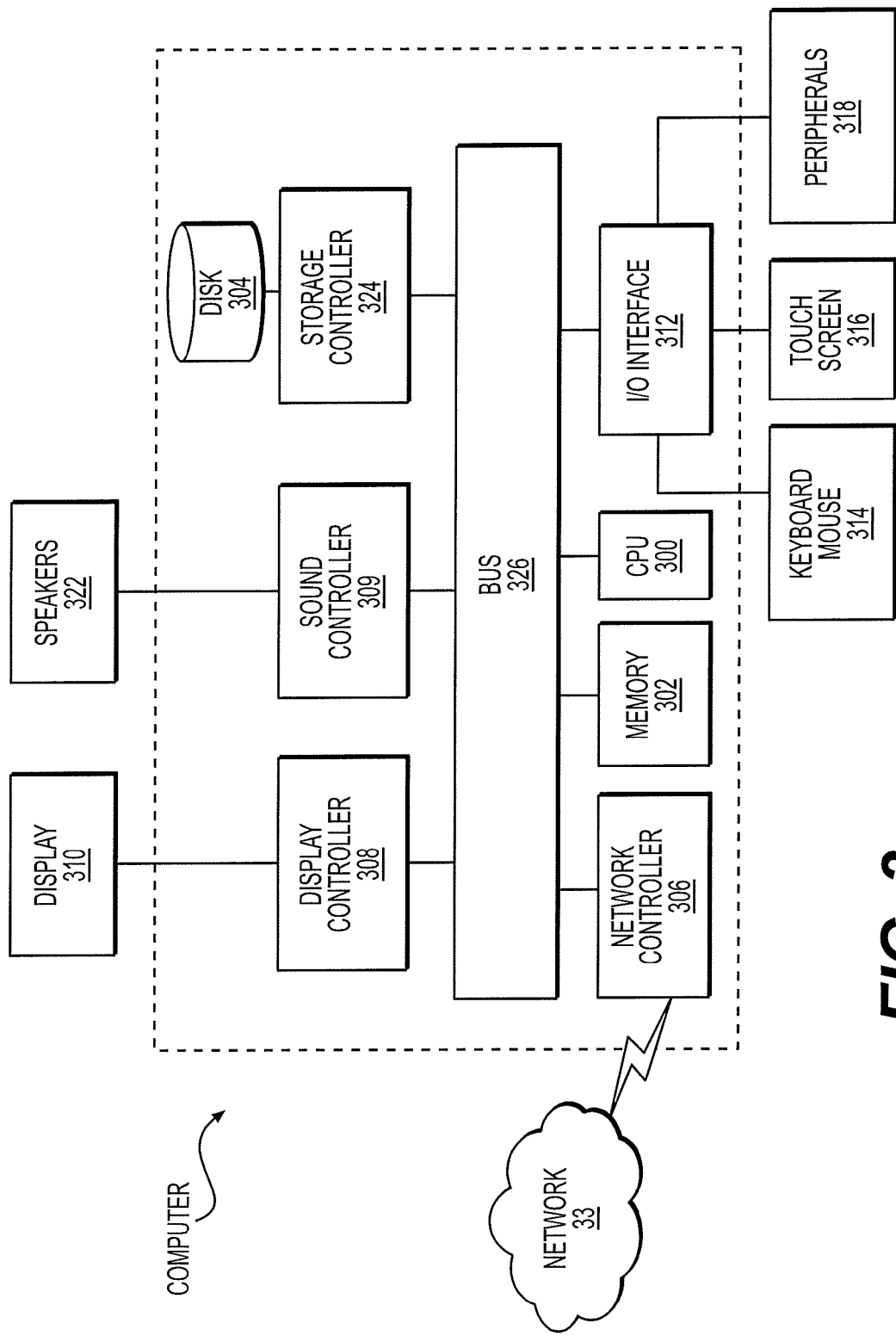
FIG. 3 shows the elements present in an embodiment of the computer.

A hardware description of the computer according to exemplary embodiments is described with reference to FIG. 3 (Yakovlev, A. A. et al., US Patent Application US20130215979 A1—incorporated herein by reference in its entirety). In FIG. 3, the computer includes a CPU 300 which performs the processes described above. The process data (e.g. the detected pressure of the bladder) and instructions (e.g. alert settings, time intervals to micturate) may be stored in memory 302. These processes and instructions may also be stored on a storage medium disk 304 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computer communicates, such as a server or computer.

Further, the claimed advancements may be provided as a utility application, background daemon, or component of an operating system, or combination thereof, executing in conjunction with CPU 300 and an operating system such as Microsoft Windows 7, UNIX, Solaris, LINUX, Apple MAC-OS and other systems known to those skilled in the art.

The hardware elements in order to achieve the computer may be realized by various circuitry elements, known to those skilled in the art. For example, CPU 300 may be a Xenon or Core processor from Intel of America or an Opteron processor from AMD of America, or may be other processor types that would be recognized by one of ordinary skill in the art. Alternatively, the CPU 300 may be implemented on an FPGA, ASIC, PLD or using discrete logic circuits, as one of ordinary skill in the art would recognize. Further, CPU 300 may be implemented as multiple processors cooperatively working in parallel to perform the instructions of the inventive processes described above.

The computer in FIG. 3 also includes a network controller 306, such as an Intel Ethernet PRO network interface card from Intel Corporation of America, for interfacing with network 33. As can be appreciated, the network 33 can be a public network, such as the Internet, or a private network such as an LAN or WAN network, or any combination thereof and can also include PSTN or ISDN sub-networks. The network 33 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer further includes a display controller 308, such as a NVIDIA GeForce GTX or Quadro graphics adaptor from NVIDIA Corporation of America for interfacing with display 310, such as a Hewlett Packard HPL2445w LCD monitor. A general purpose I/O interface 312 interfaces with a keyboard and/or mouse 314 as well as a touch screen panel 316 on or separate from display 310. General purpose I/O interface also connects to a variety of peripherals 318 including printers and scanners, such as an OfficeJet or DeskJet from Hewlett Packard.

A sound controller 320 is also provided in the computer, such as Sound Blaster X-Fi Titanium from Creative, to interface with speakers/microphone 322 thereby providing sounds and/or music.

The general purpose storage controller 324 connects the storage medium disk 304 with communication bus 326, which may be an ISA, EISA, VESA, PCI, or similar, for interconnecting all of the components of the computer. A description of the general features and functionality of the display 310, keyboard and/or mouse 314, as well as the display controller 308, storage controller 324, network controller 306, sound controller 309, and general purpose I/O interface 312 is omitted herein for brevity as these features are known.

The exemplary circuit elements described in the context of the present disclosure may be replaced with other elements and structured differently than the examples provided herein.

According to a second aspect, the disclosure relates to a medical device, comprising: (i) a plurality of bodies surrounding a body passage so that each body contacts the body passage for constricting at least a portion of the body passage, wherein the plurality of bodies are elastically connected to one another and enclose a space therebetween, (ii) a pressure sensor to sense a pressure on a bladder, and (iii) a computer electrically connected to the pressure sensor and the plurality of bodies, where the computer controls an electrical current that affects a magnetic force that affects a size of the space in response to signals from the pressure sensor.

In one embodiment, the body is a rectangular plate 101. In one embodiment, the plate is flat. The length of the plate may range from 0.5-4 mm, preferably 0.5-2 mm, more preferably 0.5-1.5 mm. The width of the plate may range from 0.2-3 mm, preferably 0.2-1.5 mm, more preferably 0.2-1 mm. The thickness of the plate may range from 0.1-2 mm, preferably 0.1-1 mm, more preferably 0.1-0.5 mm. In another embodiment, the plate is curved to accommodate the curved surface of the body passage. The term "girth", as used herein, refers to a length around a curve. A girth of the plate ranges from more than 0.2 cm to 3.5 mm, preferably more than 0.2 mm to 1.7 mm, more preferably more than 0.2 to 1.2 mm. The term "chord", as used herein, refers to a straight line segment between two opposing ends of the curve. A chord of the plate ranges from 0.2-3 mm, preferably 0.2-1.5 mm, more preferably 0.2-1 mm. The term "depth of a curve", as used herein, refers to a shortest distance between the chord and a highest point of the curve. A depth of a curve of the plate may range from 0.05-0.5 mm, preferably 0.1-0.3 mm, more preferably 0.1-0.2 mm.

Similar to the plurality of bodies in the annular array of the first aspect of the disclosure, each body in the second aspect of the disclosure is attracted to the adjacent body and the attraction between each body may be provided by a magnetic force or a spring force, preferably through spring force. Once all of the adjacent bodies in a closed loop of spring-connected bodies are in contact with one another, the loop cannot get any smaller and the interior of the structure inherently remains open. The attraction between adjacent bodies may be provided by pre-stressed tension springs 102 between the bodies. The springs may be made of the aforementioned elastic and flexible biocompatible materials. There may be a spring between each body and the spring may be outside of the body. The exterior of the body may have an attachment point, such as a loop, a hole and/or a hook, for the spring, which may be attached to the body with a hook, a clamp and/or a knot. In an alternative embodiment, there is a continuous spring which connects all the bodies. This spring passes through each body and may have two free ends (e.g., in the form of loops) that can be connected to one another to form an annular prosthesis. In one embodiment, the bodies are not at fixed locations along the length of the spring. In a preferred embodiment, some or all of the bodies are secured to the spring at predetermined locations along its circumference so that when the plurality of bodies is stretched apart to allow the passage of solids and/or fluids, the bodies are equally spaced along the circumference of the spring.

Similar to the plurality of bodies in the annular array of the first aspect of the disclosure, the number of bodies in the second aspect of the disclosure may be chosen to constrict the body passage to a constricted state in which the blood circulation in the constricted wall portion is substantially unrestricted and the flow of urine is at least restricted. The number of bodies may range from 2-20, preferably 4-12, more preferably 4-10. When all the bodies are in contact with one another, the size of the space enclosed by the plurality of the bodies ranges from 1-15 mm, preferably 4-12 mm, more preferably 4-10 mm. The size of the space is the longest distance measured from a center of a first body to a center of a second body which furthest away from the first body. For adults, there are preferably 5-9 bodies, preferably 6-9 bodies, more preferably 7-9 bodies and the size of the space ranges from 5-9 mm, preferably 6-9 mm, more preferably 7-9 mm. For children and/or young adults, there are preferably 2-6 bodies, preferably 2-5 bodies, more preferably 3-5 bodies and the size of the space ranges from 2-6 mm, preferably 2-5 mm, more preferably 3-5 mm. When the plurality of bodies are stretched apart to allow the passage of solids and/or fluids, the size of the space increases by 1-30% relative to the initial size, preferably 5-20%, more preferably 10-15%. In one embodiment, the size of the space ranges from 2-19.5 mm, preferably 5-15 mm, more preferably 5-12 mm.

In a preferred embodiment, there are two rectangular plates and they are positioned at opposing portions of a curved surface of the body passage. Each plate may have at least two holes located along opposite sides of the plate. Preferably, the holes are located along opposite lengths of the plate and near the mid-point of each length (FIG. 1B). In another embodiment, there is a hole at every corner of the plate. The springs may be attached to the holes with knots, clamps and/or hooks.

Similar to the plurality of bodies in the annular array of the first aspect of the disclosure, each body in the second aspect of the disclosure comprises a magnetic core which does not need to be biocompatible because the magnetic core is coated with the aforementioned biocompatible materials. The magnetic core may take on the aforementioned shapes and dimensions. In some embodiments, a magnetic core may include two magnets with opposite polarities that attract one another. In an embodiment with two plates, a first magnetic core in the first plate may be a magnetically soft material while a second magnetic core in the second plate may be a magnetically hard material, which refers to a magnetic material that retains magnetism after being magnetized (e.g. permanent magnets) and may attract the first magnetic core. Therefore, the first plate may be attracted to the second plate by magnetic forces to constrict the body passage. Preferably, both plates can move toward each other. The springs connecting the both plates may be pre-stressed compression springs, which provide a counter force to balance the attractive magnetic force so that the plates do not flatten the body passage. The first plate may also comprise a coil of wire, preferably made of the aforementioned grades of stainless steel, wound around the plate to facilitate the reversal of a magnetic polarity of the first plate. The coil of wire may be connected to a rechargeable battery in the computer to reverse the magnetic polarity of the first plate, which then repels the second plate and allowing solids and/or fluids to pass through the body passage. Preferably, both plates move apart from each other. The diameter of the wire ranges from 0.01-1 mm, preferably 0.025-0.2 mm, more preferably 0.025-0.1 mm. There may be 10-200 coils around the plate, preferably 50-150 coils, more preferably 80-120 coils. The coils may be wrapped lengthwise or, preferably, breadthwise around the plate.

The aforementioned descriptions of the pressure sensor and the computer of the medical device of the first aspect are also relevant to the medical device of the second aspect of the disclosure.

The third aspect of the disclosure relates to a method for treating urinary incontinence in a patient, comprising: (i) implanting the plurality of bodies of the medical device of the first aspect around a portion of the urinary tract, (ii) implanting the pressure sensor of the medical device of the first aspect to detect a pressure of the bladder with the pressure sensor, (iii) communicating a detected pressure to the computer of the medical device of the first aspect, which alerts the patient when the detected pressure rises above a predetermined threshold value, and (iv) expanding the annular array to discharge urine through the urethra when the detected pressure exceeds the predetermined threshold value, or (v) contracting the annular array to prevent urine discharge from the urethra when the detected pressure is less than the predetermined threshold value.

The plurality of bodies and the pressure sensor may be implanted in animals, pediatric and adult patients. For human patients, the internal device may be implanted through transurethral access in males and transvaginal access in females. The plurality of bodies may surround and constrict the urethra. Preferably, the plurality of bodies may be implanted at the neck of the bladder or below the prostate (bulbar urethra) in males or around the external urethral sphincter in females. It may be desirable to first measure or "size" the outer circumference of the body passage where the plurality of bodies is to be implanted. For example, the outer diameter of the urethra is about 8 mm for male patients, about 6 mm for female patients and about 3 mm for pediatric patients. The measurement may be performed using one or more sizing instruments that are known to those skilled in the art. When the desired size has been determined, an annular array of that size may be implanted. Annular arrays having different sizes may be provided by, for example, producing arrays with different numbers of a given size body, or by using bodies of different sizes to make arrays of different sizes. Initially, the movements of the annular array may be calibrated by using the computer to control the amplitude of the magnetic force generated by a magnetized ring. During the calibration process, the expansion and/or contraction of the annular array, and hence the extent of constriction of the wall portion of the urethra, ureter, renal pelvis or the neck of the bladder, is adjusted until the desired restriction of the flow of urine is obtained.

The implanted elements (i.e. the plurality of bodies, ring and/or the pressure sensor) may comprise a medication to promote tissue healing. The medication may be stored in a microchip, which is attached to the elements. The medication may also be in a form of a paste, which is applied onto the elements. Preferably, the medication is applied onto a patch, which can stick on the elements. The patch may be made of a bioabsorbable material, such as alpha-polyesters or poly- (alpha-hydroxy) acids, which degrade with the healing process so that the medication is transferred to the healing tissue. The medication may include an antibiotic to combat infection, and/or the medication may include a steroid to promote appropriate healing.

The pressure sensor may be implanted at the aforementioned locations on the bladder. The communication between the pressure sensor and the computer may occur by the aforementioned methods. The pressure sensor may be programmed to detect the pressure of the bladder every 10-60 minutes, preferably 10-30 minutes, more preferably 10-20 minutes. When the pressure detected by the pressure sensor exceeds the predetermined threshold level, the computer alerts the patient. The computer may emit a sound (for example, a message or a tune) and/or light and/or display a message and/or vibrate. In one embodiment, there is a vibrator implanted subcutaneously, near the internal control unit of the computer.

The patient may then activate the expansion of the annular array by selecting this option on the computer. The option may be displayed on the computer screen. Subsequently, the computer initiates a current flow in the coil of wire to magnetize the ring, which then attracts the plurality of bodies toward the ring and away from the center of the annular array. The diameter of the annular array may expand by 0.5-4.5 mm, preferably 0.5-3 mm, more preferably 1-2 mm. After the expansion of the annular array, urine can be discharged from the urethra, resulting in a decrease of the bladder pressure. The patient may then select an option to contract the annular array. The computer then demagnetizes the ring to remove the magnetic force applied on the annular array, thus allowing the springs in the annular array and the springs between each body and the ring to urge the plurality of bodies toward the center of the annular array. In this arrangement, constriction of the urethra is achieved.

The fourth aspect of the disclosure relates to a method for treating urinary incontinence in a patient, comprising: (i) implanting the plurality of bodies of the medical device of the second aspect around a portion of the urinary tract, (ii) implanting the pressure sensor of the medical device of the second aspect to detect a pressure of the bladder with the pressure sensor, (iii) communicating a detected pressure to the computer of the medical device of the second aspect, which alerts the patient when the detected pressure rises above a predetermined threshold value, and (iv) increasing the size of the space to allow urine to discharge through the urethra when the detected pressure exceeds the predetermined threshold value, or (v) decreasing the size of the space to prevent urine discharge from the urethra when the detected pressure is less than the predetermined threshold value.

The aforementioned parameters, operating sequence and mechanism relevant to the third aspect are also relevant to this fourth aspect of the disclosure. For example, when the patient activates the expansion of the plurality of the bodies, the increase in the size of the space enclosed by the plurality of the bodies may range from 0.5-4.5 mm, preferably 0.5-3 mm, more preferably 1-2 mm to allow the urine to discharge from the urethra. The patient may then select an option to contract the space. The computer then demagnetizes the first plate to remove the repulsive magnetic force between the first and second plates, thus allowing the springs between the plates and the attractive magnetic force between the first and second plate to urge the plates to their initial position to constrict the urethra.

The invention claimed is:

1. A medical device, comprising:
a plurality of rectangular plates configured to surround a body passage so that each rectangular plate contacts the body passage for constricting at least a portion of the body passage, wherein the plurality of rectangular plates are elastically connected to one another by a spring, and, together with the spring, form an annular prosthesis to enclose a space therebetween;
a pressure sensor to sense a pressure on a bladder;
a computer electrically connected to the pressure sensor and the plurality of rectangular plates, wherein the computer controls an electrical current that affects a magnetic force that affects a size of the space in response to signals from the pressure sensor;
wherein each of the plurality of rectangular plates comprises a curve configured to accommodate a curved surface of the body passage;
wherein each rectangular plate has a chord, measured as a straight line distance between opposing ends of the curve, of 0.2 to 1.5 mm; and
wherein each rectangular plate has a curve depth, measured as a shortest distance between the chord and a highest point of the curve, of more than 0.1 mm and up to 0.3 mm.

2. The medical device of claim 1, wherein the plurality of rectangular plates comprises two rectangular plates positioned at opposing portions of a curved surface of the body passage.

3. The medical device of claim 2, wherein the computer controls a magnetic polarity of one of the two rectangular plates.

4. The medical device of claim 3, wherein:
each rectangular plate has an embedded magnetic core coated with a biocompatible material,
the embedded magnetic core of one of the two rectangular plates is made of a magnetically soft material that does not have polarities and is magnetizable in the presence of an external magnetic field and is demagnetizable in the absence of the external magnetic field, and
the embedded magnetic core of the other of the two rectangular plates is made of a magnetically hard material that retains magnetism after being magnetized.

5. The medical device of claim 4, wherein the magnetically soft material is an alloy of iron and nickel.

6. The medical device of claim 4, wherein a volume of the magnetic core embedded within each of the two rectangular plate is 40 to 50% of a total volume of the rectangular plate.

7. A method for treating urinary incontinence in a patient, comprising:
implanting the plurality of rectangular plates of the medical device of claim 1 around a portion of a urethra;
implanting the pressure sensor to detect a pressure of the bladder with the pressure sensor;
communicating a detected pressure to the computer, which alerts the patient when the detected pressure rises above a predetermined threshold value;
increasing the size of the space to allow urine to discharge through the urethra when the detected pressure exceeds the predetermined threshold value; and
decreasing the size of the space to prevent urine discharge from the urethra when the detected pressure is less than the predetermined threshold value.

8. The medical device of claim 1, wherein each rectangular plate has a girth, measured as a length around the curve, of more than 0.2 mm and up to 1.7 mm.

9. The medical device of claim 1, wherein the spring is continuous and elastically connects all of the rectangular plates.

10. The medical device of claim 9, wherein the plurality of rectangular plates are equally spaced along a circumference of the spring.

11. The medical device of claim 9, wherein each rectangular plate has two holes located on opposite sides of the plate near a mid-point of the length of the rectangular plate, and wherein the spring is threaded through the two holes of each plate.

12. The medical device of claim 1, wherein each rectangular plate has an embedded magnetic core coated with a biocompatible material.

13. The medical device of claim 12, wherein the embedded magnetic core of each rectangular plate is made of a magnetically soft material that does not have polarities and is magnetizable in the presence of an external magnetic field and is demagnetizable in the absence of the external magnetic field.

14. The medical device of claim 13, wherein the magnetically soft material is an alloy of iron and nickel.

15. The medical device of claim 12, wherein a volume of the magnetic core embedded within each rectangular plate is 40 to 50% of a total volume of the rectangular plate.

\* \* \* \* \*